United States Patent [19]
Smith et al.

[11] Patent Number: 5,427,941
[45] Date of Patent: Jun. 27, 1995

[54] ACTINOMADURA BRUNNEA VAR. ANTIBIOTICA STRAINS

[75] Inventors: Elizabeth B. Smith, Plainsboro; Hanan K. Munayyer, West Caldwell; Michael J. Ryan, West Milford; George H. Miller, Montville, all of N.J.

[73] Assignee: Schering Corporation, Kenilworth, N.J.

[21] Appl. No.: 24,896

[22] Filed: Mar. 1, 1993

Related U.S. Application Data

[60] Continuation of Ser. No. 751,595, Aug. 21, 1991, abandoned, which is a continuation of Ser. No. 528,005, May 23, 1990, abandoned, which is a division of Ser. No. 763,742, Aug. 8, 1985, abandoned.

[51] Int. Cl.$^6$ ................................ C12N 1/20
[52] U.S. Cl. ...................... 435/252.1; 435/822
[58] Field of Search ..................... 435/252.1, 822

[56] References Cited

U.S. PATENT DOCUMENTS

| | | | |
|---|---|---|---|
| 4,551,533 | 11/1985 | Lee | 435/825 |
| 4,578,271 | 3/1986 | Kiyoto | 435/825 |
| 4,615,975 | 10/1986 | Tunac | 435/825 |
| 4,752,605 | 6/1988 | Patel et al. | 435/64 |

FOREIGN PATENT DOCUMENTS 7150390  9/1982  Japan ................... 435/825

OTHER PUBLICATIONS

Horan et al., Int. J. Systematic Bacteriol, vol. 32 1982, pp. 195–200.
Rose, A H, "Industrial Microbiology", 1961, Butterworths, pp. 191–201.

Primary Examiner—Irene Marx
Attorney, Agent, or Firm—Eric S. Dicker; John J. Maitner; Matthew Boxer

[57] ABSTRACT

7-Chloro-8-methoxytetracycline isolated from antibiotic ES-119 and antibiotic Tet. 7 which are produced by fermentation of mutants of *Actinomadura brunnea*, namely *Actinomadura brunnea* var. *antibiotica*, ATCC 53108 and *Actinomadura brunnea* var *antibiotica* ATCC 53180 and its use as an antibiotic against gram-positive and gram-negative organisms are disclosed.

2 Claims, 2 Drawing Sheets

ACTINOMADURA BRUNNEA VAR. ANTIBIOTICA STRAINS

This application is a continuation of application Ser. No. 07/751,595 filed Aug. 21, 1991, now abandoned, which is a continuation of application Ser. No. 07/528,005 filed May 23, 1990, now abandoned, which is a division of application Ser. No. 06/763,742 filed Aug. 8, 1985, now abandoned.

BACKGROUND OF THE INVENTION

This invention relates to a new tetracycline antibiotic, 7-chloro-8-methoxytetracycline, isolated from antibiotics designated as antibiotic ES-119 and antibiotic Tet. 7, which are produced by fermentation under controlled conditions using biologically pure cultures of the new microorganisms, *Actinomadura brunnea* var. *antibiotica* var. nov. ATCC 53108 and *Actinomadura brunnea* var. antibiotica ATCC 53180, respectively.

In a related, commonly-assigned, co-pending application which is U.S. Ser. No. 763,740 filed Aug. 8, 1985, now abandoned, filed on even date herewith, another new tetracycline 7-chloro-8-methoxy-2'-N-methyltetracycline, produced by fermentation of *A. brunnea* ATCC 39216 is disclosed.

In another related, commonly-assigned, co-pending application now U.S. Pat. No. 4,752,605, filed on even date herewith, another new tetracycline, 7-chloro-4a-hydroxy-8-methoxytetracycline, produced by fermentation of *Dactylosporangium vescum* ATCC 39499 is disclosed.

SUMMARY OF THE INVENTION

The present invention embraces the biologically pure culture of the microorganism *Actinomadura brunnea* var. *antibiotic* var. nov. having the identifying characteristics of ATCC 53108 as well as mutants and variants thereof, said culture being capable of producing antibiotic ES-119 comprising the compound of this invention, 7-chloro-8-methoxytetracycline, in a recoverable quantity upon fermentation under aerobic conditions in an aqueous medium containing assimilable sources of nitrogen and carbon.

The present invention also embraces the biologically pure culture of the microorganism *Actinomadura brunnea* var. *antibiotica* var. nov. having the identifying characteristics of ATCC 53180 as well as routants and variants thereof, said culture being capable of producing antibiotic Tet. 7 comprising the compound of this invention, 7-chloro-8-methoxytetracycline, in a recoverable quantity substantially free from 7-chloro-8-methoxy-2'-N-methyltetracycline, upon fermentation under aerobic conditions in an aqueous medium containing assimilable sources of nitrogen and carbon.

The present invention is also directed to antibiotic ES-119 and antibiotic Tet. 7 and to one component thereof, namely 7-chloro-8-methoxytetracycline, represented by the formula:

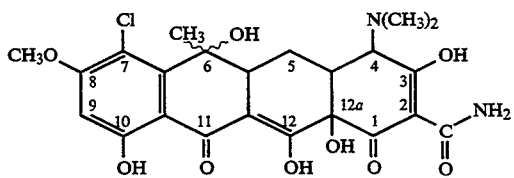

or a pharmaceutically acceptable salt thereof.

The compound of this invention is systematically named 7-chloro-4-dimethylamino-8-methoxy-1,4,4a,5-,5a,6,11,12a-octahYdro-3,6,10,12,12a-pentahydroxy-6-methyl-1,11-dioxo-2-naphthacene carboxamide or more simply named 7-chloro-8-methoxytetracycline which hereinafter will be used.

The present invention is directed to a pharmaceutical composition comprising an antibiotically effective amount of 7-chloro-8-methoxytetracycline or a pharmaceutically acceptable salt thereof and a pharmaceutically acceptable carrier or diluent.

The present invention, in addition, is directed to a method of eliciting an antibiotic effect in a host, e.g., a mammal, having a susceptible infection which comprises administering to said host an antibiotically effective amount of 7-chloro-8-methoxytetracycline or a pharmaceutical composition thereof.

DETAILED DESCRIPTION OF THE INVENTION

ISOLATION AND PURIFICATION OF THE ANTIBIOTIC ES-119

Figure 1:
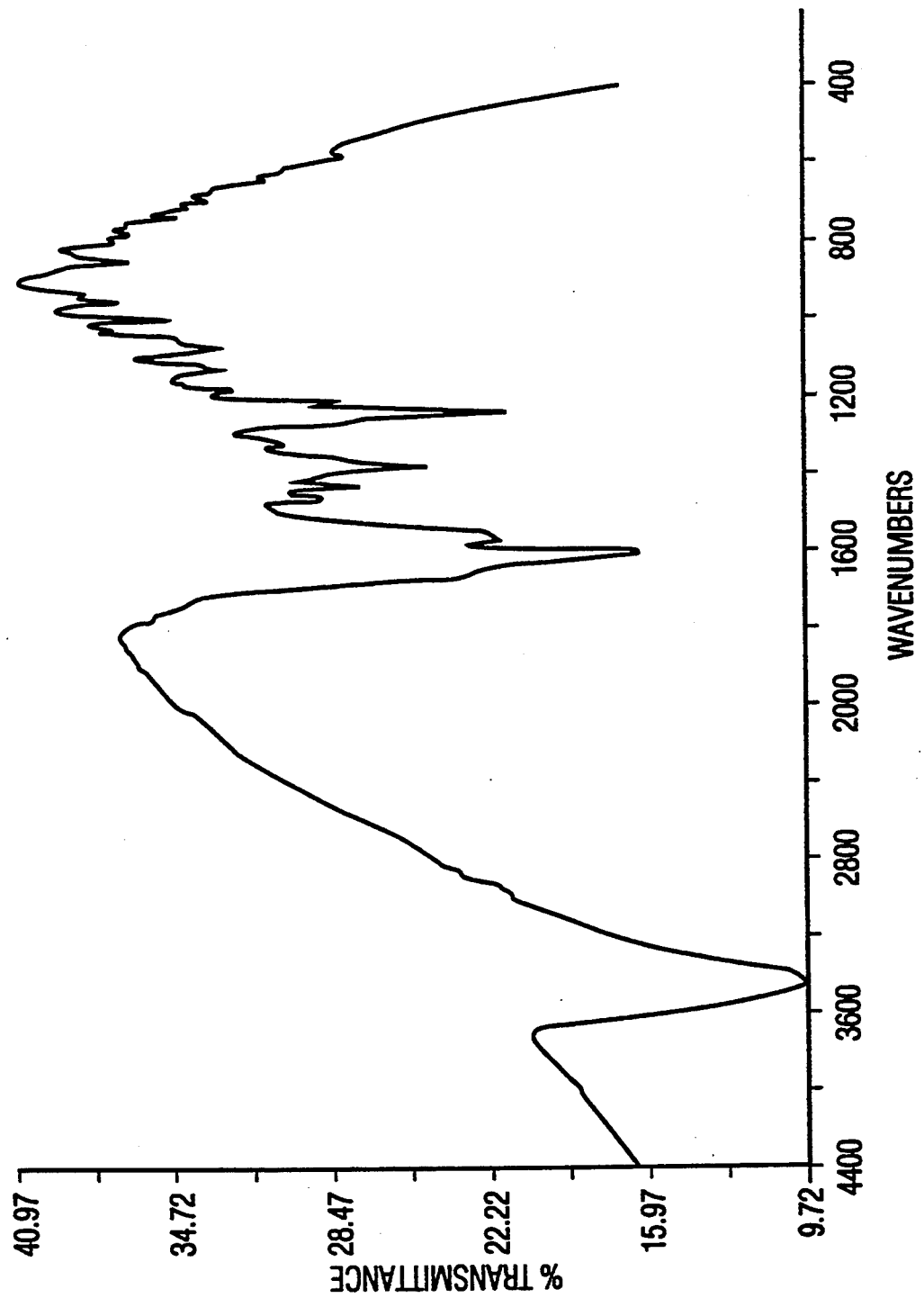
FIG. 1 is the infrared spectrum of 7-chloro-8-methoxytetracycline.

Antibiotic ES-119 is produced when the elaborating microorganism, *Actinomadura brunnea* var. *antibiotica* var. nov. having the identifying characteristics of ATCC 53108 is grown in an appropriate medium.

Antibiotic ES-119 may be isolated from the fermentation broth by employing the following procedures:

(a) Adjust the pH of the whole broth to 2 and separate the roycelia from a solution containing antibiotic ES-119 and other biologically inactive organic compounds;

(b) Separate said solution into a solution containing antibiotic ES-119 and liquor containing biologically inactive organics; and (c) Remove the solvents from the solution containing antibiotic ES-119 to produce a antibiotic ES-119 as a solid residue.

On a small scale, the separation in step (b) is normally accomplished by solvent extraction of said solution using one volume of an organic solvent (e.g. n-butanol saturated with water) each time for each volume of said solution. On a larger (preparative) scale, column chromatography on a neutral resin (e.g. XAD-2,-4 or -16, a neutral polystyrene resin available from Rohm and Haas, Philadelphia, Pa.) eluting with aqueous alcohol mixtures (e.g., 25%, 50% methanol in water and 100% methanol) and an alcohol containing dilute aqueous mineral acid (e.g., methanol:0.02N HCl) is normally employed to remove the biologically inactive organics and produce an eluate containing the antibiotic ES-119.

ISOLATION AND PURIFICATION OF THE ANTIBIOTIC Tet. 7

Antibiotic Tet. 7 is produced when the elaborating microorganism, *Actinomadura brunnea* var. *antibiotica* var. nov. having the identifying characteristics of ATCC 53180 is grown in an appropriate medium.

Antibiotic Tet. 7 may be isolated from the fermentation broth by employing the procedures described hereinabove in reference to antibiotic ES-119.

PURIFICATION OF THE ANTIBIOTIC ES-119 AND ANTIBIOTIC TET. 7 AND ISOLATION OF 7-CHLORO-8-METHOXYTETRACYCLINE

The antibiotic ES-119 is made up of at least two active (tetracycline) components (in about an 60:40 ratio), so no meaningful physico chemical data can be obtained for the antibiotic ES-119.

The major (60%) active component isolated from antibioic ES-119 was identified as 7-chloro-8-methoxy-2′-N-methyltetracycline (which is the subject of commonly-assigned, co-pending U.S. patent application Ser. No. 07/528,006, filed May 23, 1990, which is a continuation of Ser. No. 06/763,740, filed Aug. 8, 1985, now abandoned. The other active component isolated was characterized as the novel 7-chloro-8-methoxy-tetracycline of this invention.

The active antibiotics including the 7-chloro-8-methoxytetracycline of this invention can be separated from antibiotic ES-119 by chromatography using, for example, high performance reverse-phase liquid chromatography on $C_{18}$ columns e.g. μ-Bondapak $C_{18}$, or Sephadex G-25 gel column chromatography. For large scale preparation, use of a Sephadex G-25 gel column chromatography is preferred. The eluate from the chromatography column was monitored by disc testing the activity of each fraction against *B. subtills*, ATCC 6633 and *E. coli*, OLA 290R5. The desired active fractions were pooled and lyophilized to give the 7-chloro-8-methoxytetracycline of this invention and 7-chloro-8-methoxy-2′-N-methyltetracycline.

The antibiotic Tet. 7 contains almost exclusively 7-chloro-8-methoxytetracycline substantially free (i.e., less than about 1%) of 7-chloro-8-methoxy-2′-N-methyltetracycline. Purification of antibiotic Tet. 7 and isolation of 7-chloro-8-methoxytetracline is performed by using procedures described hereinabove in reference to antibiotic ES-119.

The physical and spectroscopic data for 7-chloro-8-methoxytetracycline are presented in Table I hereinbelow.

TABLE I
PHYSICO-CHEMICAL DATA FOR 7-CHLORO-8-METHOXYTETRACYCLINE (a) The Fast Atom Bombardment mass spectrum (FAB-MS) in glycerol yielded an M+H peak at 509.1284. This corresponds to the formula $C_{23}H_{26}N_2O_9Cl$ which calculates for the exact mass, 509.1327.

(b) The ultraviolet absorption maxima in methanol are: 235 (ε 15,400), 249 (ε 14,300) and 374 nm (ε 17,100). The ultraviolet absorption maxima shift to 233 (ε 16,500), 258 (ε 16,100) and 370 nm (ε 16,200) upon the addition of acid. The maxima shift to 241 (ε 17,900), 280 (ε 12,800) and 385 nm (ε 16,600) upon the addition of base.

(c) The infrared spectrum in KBr is shown in FIG. 1. The characteristic absorption bands are the following: 3530 (br), 1650, 1610, 1580, 1380 and 1240 $cm^{-1}$.

Figure 2:
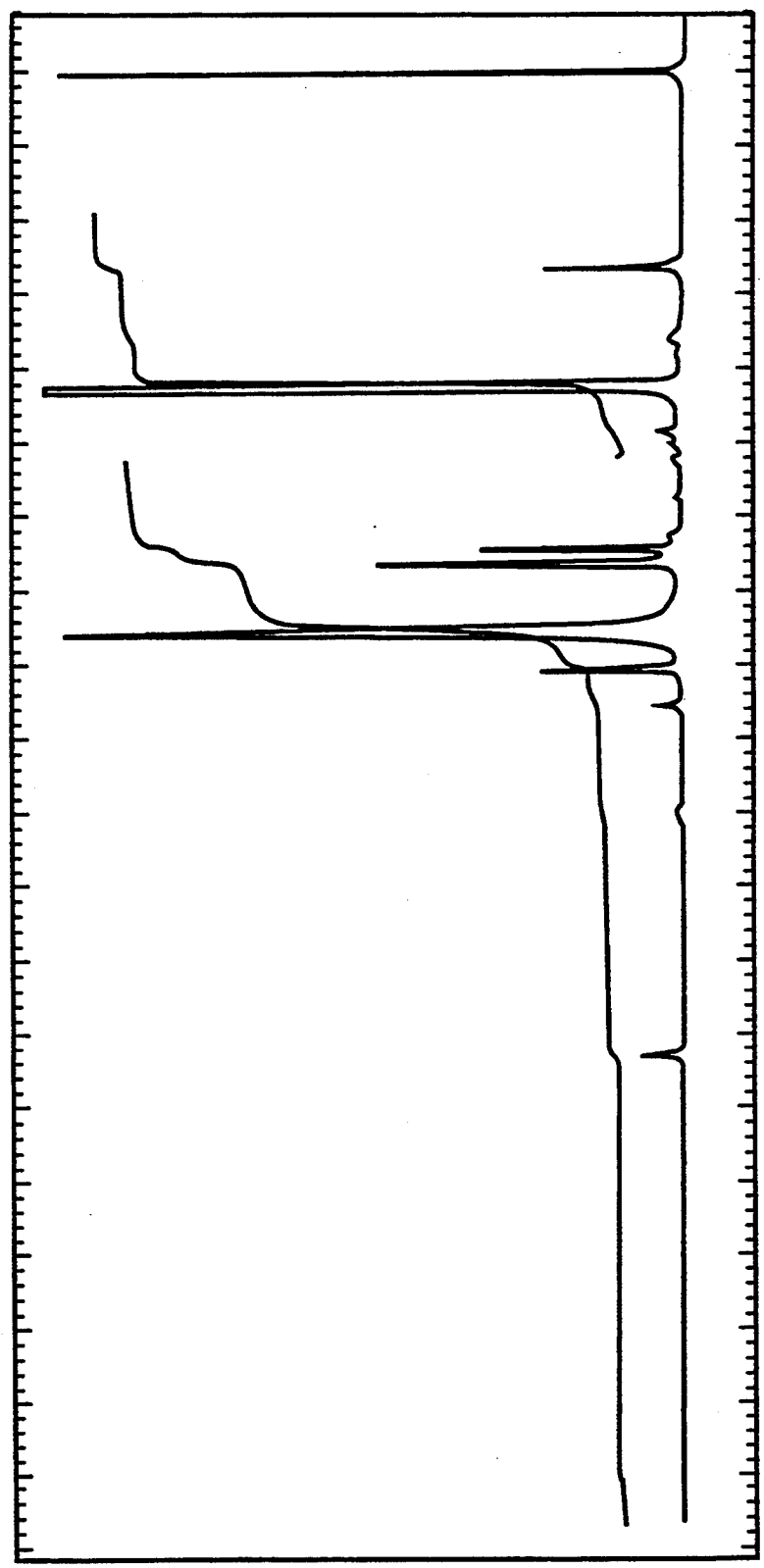
FIG. 2 is the $^1$H NMR spectrum of 7-chloro-8-methoxytetracycline.

(d) The ¹H-NMR in acetone-$d_6$ and methanol-$d_4$ is shown in FIG. 2.

(3) The $^{13}C$-NMR of spectral data for 7-chloro-8-methoxytetracycline, 7-chloro-8-methoxy-2 ′-N-methyltetracycline and 7-chlorotetracycline are presented in Table II.

TABLE II
$^{13}C$-NMR IN DMSO-$d_6$ FOR 7-CHLORO-8-METHOXY-TETRACYCLINE (COMPOUND A) 7-CHLORO-8-METHOXY-2′-N-METHYLTETRACYCLINE (COMPOUND B) AND 7-CHLOROTETRACYCLINE (COMPOUND C)

| Carbon | Resonance (PPM) | | |
|---|---|---|---|
| | Compound A | Compound B | Compound C |
| C-1 | 194.0 | 193.1 | 193.4 |
| C-2 | 95.3 | 96.5 | 95.6 |
| CONHR | 171.9 | 169.9 | 172.1 |
| | (R = H) | (R = CH₃) | (R = H) |
| C-3 | 187.3 | 186.3 | 187.3 |
| C-4 | 68.3 | 68.0 | 68.1 |
| N(CH₃)₂ | 41.5ᵃ | 41.5ᵃ | 41.0ᵃ |
| C-4a | 34.4 | 34.8 | 34.9 |
| C-5 | 27.0 | 26.9 | 27.1 |
| C-5a | 42.4ᵃ | 42.3ᵃ | 42.0ᵃ |
| C-6 | 73.4 | 73.3 | 70.4 |
| C-6-CH₃ | 20.5 | 20.4 | 25.0 |
| C-6a | 148.5 | 148.5 | 143.6 |
| C-7 | 111.6 | 111.6 | 121.2 |
| C-8 | 163.3 | 163.2 | 139.7 |
| | (OCH₃)ᵇ | (OCH₃)ᵇ | (H)ᵇ |
| C-9 | 100.1 | 100.0 | 118.9 |
| C-10 | 161.9 | 161.8 | 160.7 |
| C-10a | 111.6 | 108.6 | 117.0 |
| C-11 | 190.5 | 190.6 | 193.4 |
| C-11a | 105.6 | 105.4 | 106.1 |
| C-12 | 174.3 | 174.1 | 175.7 |
| C-12a | 73.9 | 73.6 | 73.2 |
| O—CH₃ | 57.0 | 56.9 | — |
| N—CH₃ (2′-N) | — | 26.5 | — |

ᵃ - indicates peaks buried under DMSO peak, but observed when spectrum was run in D₂O/Dioxane.
ᵇ - the shift of the C-8 carbon from 139.7 ppm in 7-chlorotetracycline, Compound C, to 163 ppm in 7-chloro-8-methoxytetracycline, Compound A, indicates the presence of an O—CH₃ group Based on the above physico-chemical data, the structure of compound of this invention (without specific stereochemistry) is the following:

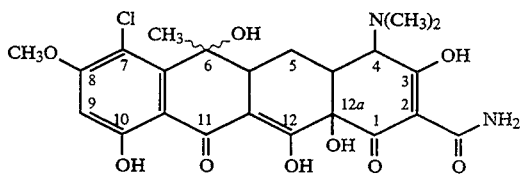

BIOLOGICAL PROPERTIES OF ANTIBIOTIC ES-119 ANTIBIOTIC Tet. 7 AND 7-CHLORO-8-METHOXYTETRACYCLINE

The antibiotic ES-119 and antibiotic Tet. 7 and the common component of each, 7-chloro-8-methoxytetracycline were tested in vitro and found to be active against a variety of gram-positive and gram,negative bacteria.

In comparative in-vitro antibacterial activity tests performed via conventional microtiter dilution methods in Mueller-Hinton broth, 7-chloro-8-methoxytetracycline showed activity against 91 gram-positive (tetracycline-susceptible) organisms with a Geometric Mean Minimum Inhibitory Concentration (GMM, mcg/mL) of 0.12 which is similar to the GMM for tetracycline (0.46) and to the GMM for 7-chloro-8-methoxy-2′-N-methyltetracycline (0.36). The compound of this invention had a GMM of 4.2 against 23 gram-negative (tetracycline-susceptible) organisms compared to a GMM of 2.3 for tetracycline and 33.0 for 7-chloro-8-methoxy-2'-N-methyl-tetracycline which is disclosed in commonly-assigned, co-pending U.S. patent application Ser. No. 763,740 filed Aug. 8, 1985. The twenty-three gram-negative organisms included 9 strains of *E. coli;* 8 strains of *Klebsiella;* 4 strains of *Enterobacter* and 2 strains of *Salmonella.* The compound of this invention (7-chloro-8-methoxytetracycline) exhibited a GMM of 0.21 against 9 Methicillin resistant *Staphylococci*, a GMM of 0.14 against 54 Methicillin-suspectible *Staphylococci* organisms, a GMM of 0.06 against 25 *Streptococci* (including Groups A, B, C, G; *S. pneumoniae, S. viridans, S. faecium* and *S. faecalis*), and a GMM of 0.16 against 10 strains of *Bacteroides fragilis* (tested in Mueller-Hinton agar with 5% sheep blood).

The present invention contemplates a method of eliciting an antibacterial effect in a host, e.g., a warm-blooded mammal such as a human being having a susceptible bacterial infection which comprises administering to said host an antibiotically effective amount of 7-chloro-8-methoxytetracycline or a pharmaceutical composition thereof. By the term "eliciting" is meant treating or preventing susceptible bacterial infection.

The methods of this invention are implemented using pharmaceutical compositions comprising a pharmaceutically acceptable carrier and a therapeutically effective quantity of 7-chloro-8-methoxytetracycline or a pharmaceutically acceptable salt thereof.

The preferred pharmaceutically acceptable salts are the acid addition salts. Pharmaceutically acceptable acid addition salts of 7-chloro-8-methoxytetracycline are those formed from strong acids containing pharmaceutically acceptable anions, such as hydrochloride, hydrobromide, hydrogen sulfate or trichloroacetate. Acid addition salts may also be formed with carboxylic acids having 2–18 carbon atoms such as aliphatic, cycloaliphatic, aromatic and heterocyclic carboxylic acids, including dicarboxylic acids. Exemplary of such acids are acetic, propionic, stearic, tartaric, maleic, cyclopropylcarboxylic cyclopentylcarboxylic, adamantoic, furic, nicotinic, thenoic, picolinic, benzoic, phenylacetic and the like.

The antibiotic may be combined with any suitable pharmaceutical carrier and administered orally, parenterally or topically in a variety of formulations. For oral administration, the antibiotics of this invention may be compounded in the form of tablets, capsules, elixirs or the like. Tablets and capsules may contain such excipients as starch or lactose; liquid oral forms may contain coloring or flavoring agents. Topical preparations may be in the form of creams, hydrophobic and hydrophylic ointments, or aqueous, non-aqueous or emulsion-type lotions. Typical carriers for such formulations are water, oils, greases, polyesters and polyols. Parenteral formulations, e.g., injectable dosage forms, are usually liquids such as solutions or suspensions, with typical carriers being distilled water or saline solution. Oral administration of the compound of this invention or pharmaceutical compositions thereof is preferred.

The dose to be administered in any particular dosage form will be determined by the attending clinican after consideration of various factors, such as the age and condition of the animal species being treated, the susceptibility of the infecting organism to the antibiotic, the stage and severity of the infection.

Generally, the oral dosage for humans ranges from about 1.0 mg per kilogram of body weight per day to about 25 mg per kilogram of body weight per day, in single or divided doses, with about 5 mg per kilogram to about 10 mg per kilogram being preferred.

Generally, the parenteral dosage for humans ranges from about 100 mg per day to about 2000 mg per day, in single or divided doses, with about 500 mg to about 1000 mg per day being preferred.

Generally, the topical dosage form for humans contains about 1% to about 5% with about 1% to about 3% being preferred.

In treating certain patients with the compounds of this invention, it is possible to include other pharmaceutically active ingredients in the same dosage unit.

The Microorganism

The microorganism used for the production of antibiotic ES-119 is a biologically pure culture of *Actinomadura brunnea* var. *antibiotica* var. nov.

A culture of this microorganism has been made a part of the collection of the American Type Culture Collection (ATCC) in Rockville, Md. where it has been assigned accession number ATCC 53108. Subcultures of *Actinomadura brunnea* var. *antibiotica* ATCC 53108 are available to the public without restriction. Use of the microorganism is dependent on U.S. Patent Laws.

The microorganism used for the production of antibiotic ES-119 was produced by exposure of a spontaneous mutant of a culture *Actinomadura brunnea* ATCC 39216 to mutagenic agent, e.g., N-methyl-N-nitro-N-nitroso-guandinine. Representatives of the mutagenized population of *Actinomadura brunnea*, were plated and allowed to grow. Two replicate agar plates (such as starch yeast agar plates) were prepared and the mutagenized populations were allowed to grow until single colonies were observed. Usually after about four days, single colonies were observed and thereafter one of the replicate plates was directly overlaid with agar containing an appropriate gram-negative indicating organism, e.g., *E. coli,* OLA 290R5. The desired mutant colonies of *Actinomadura brunnea* var. *antibiotica* var. nov. ATCC 53108 were recognized and recovered from the unoverlaid replicate plate by comparison with a clear zone of inhibition they exhibited against the gram-negative indicator strain on the overlaid plate. Antibiotic ES-119 produced from *A. brunnea* var. *antibiotica* ATCC 53108 comprises about a 60:40 mixture of -chloro-8-methoxy-2'-N-methyltetracycline and 7-chloro-8-methoxytetracycline; the spontaneous mutant of the parent *A. brunnea* ATCC 39216 produced about a 80:20 mixture of the two compounds.

*Actinomadura brunnea* var. *antibiotica* var. nov. has been characterized and found to have the microscopic, macroscopic, and whole cell hydrolysis properties of the genus Actinomadura.

The microorganism used for the production of antibiotic Tet. 7 is a biologically pure culture of *Actinomadura brunnea* var. *antibiotica* var. nov.

A culture of this microorganism has been made a part of the collection of the American Type Culture Collection (ATCC) in Rockville, Md. where it has been assigned accession number ATCC 53180. Subcultures of *Actinomadura brunnea* var. *antibiotica* ATCC 53180 are available to the public without restriction. Use of the microorganism is dependent on U.S. Patent Laws.

The microorganism used for production of Tet. 7 was produced by exposure of a high level streptomycin-resistant mutant isolated from a culture *Actinomadura brunnea* ATCC 39216 to a mutagenic agent, e.g., N-methyl-N-nitro-N-nitroso-guandinine. Representative of the mutagenized population of *Actinomadura brunnea* were allowed to grow on 600 agar plates such as starch yeast agar until single colonies had grown to 3 to 4 mm in diameter. Thereafter, all 600 plates were directly overlaid with agar containing an appropriate gram-negative indicating organism, e.g., *E. coli*, OLA 290R5. The desired mutant colonies of *Actinomadura brunnea* var. *antibiotica* var. nov. were recognized by the clear zone where the gram-negative indicator strain was unable to grow. A spontaneous tetracycline-resistant derivative was selected and designated as antibiotic Tet-7. Antibiotic Tet. 7 comprises 7-chloro-8-methoxytetracycline containing less than about 1% of 7-chloro-8-methoxy-2'-N-methyltetracycline.

Description of the Producing Strains

*Actinomadura brunnea* var. *antibiotica* var. nov. ATCC 53108 and ATCC 53180

The taxonomic methods used herein are those cited by R. E. Gordon and V. Blanchard, "Some criteria for the recognition of *Nocardia madura*", *J. Gen Microbiol.*, 45, pp 355–364 (1966), Luedemann and Brodsky, "*Micromonospora carbonacea* sp. nov., an everninomicin-producing organism," Antimicrob Agents Chemotherapy, pp 47–52, 1964; Horan and Brodsky, "A Novel Antibiotic-Producing *Actinomadura, Actinomadura kijaniata* sp. nov.", *International Journal Syst. Bacteriol.*, Vol. 32, pp 195–200, 1982; Becker et al, "Chemical Composition of Cell Wall Preparations from Strains of Various Genera of Aerobic Actimomycetes", *Applied Microbiology*, Vol. 13, pp 236–243, 1966; Lechevalier and Lechevalier, "Chemical Composition as a Criteria in Classification of Aerobic Actinomycetes", *International Journal Syst. Bacteriol.* Vol. 20, pp 487–493, 1970; Shirling and Gottlieb, "Methods for Characterization of Streptomyces Species", *International Journal Syst. Bacteriol*, Vol. 16, pp 313–340, 1966; and Waksman, *The Actinomycetes* Vol. 2, (The Williams & Wilkins Co., Baltimore, Md., 1961).

TABLE III

Macroscopic and Microscopic Characteristics of *Actinomadura brunnea* var. antibiotica ATCC 53108 and ATCC 53180

| Macroscopic Characteristics of ATCC 53108 | Microscopic Characteristics of ATCC 53108 and ATCC 53180 |
|---|---|
| Aerial Mycelia are formed | |
| Good growth occurs after 14–21 days at 30° C. on most rich organic media with production of brown diffusible pigments. White to gray aerial mycelia are formed on yeast extract-malt extract agar (ISP-2) and starch yeast agar. Vegetative mycelial pigments usually range in color from tan to dark brown. | Long, branching aerial mycelia, 0.5 to 0.8 microns in diameter are formed on water agar after 10 to 14 days at 30° C. The aerial mycelia fragment into long, straight to flexous chains of greater than 20 elliptical spores, 0.8 to 1.2 microns in diameter by 1.0 to 2.0 microns in length. |

Macroscopic Characteristics of ATCC 53180

Good growth occurs after 14 to 21 days at 30° C. on most rich organic media with the production of brown diffusible pigments. Pink-white to gray-white aerial mycelia are formed on several media. Vegetative mycelia pigments range in color from tan to pink to brown.

The culture characteristics of the microorganisms *Actinomadura brunnea* vat antibiotica ATCC 53108 and ATCC 53180 on various standard descriptive media are reported in Table IV. In the description of the growth characteristics of the microorganisms in Table IV, two color designators are employed. The first is a color name taken from the "Descriptive Color Name Dictionary" by Taylor, Knoche and Granville published by the Container Corporation of America (1950) U.S.A., with a color chip number corresponding to the color name, the chip number being taken from "The Color Harmony Manual,: 4th Edition, 1958, also published by the Container Corporation of America. The second designator consists of a color name and number which refers to the synonym and near synonym found in the National Bureau of Standards, Circular 553, Nov. 1, 1965 (U.S.A.).

Growth of the microorganisms, *Actinomadura brunnea* var. *antibiotica* ATCC 53108 and ATCC 53180 and *Actinomadura brunnea* ATCC 39216 on various carbon compounds is reported in Table V.

Physiologic characteristics of the microorganisms *Actinomadura brunnea* var. *antibiotica* ATCC 53108 and ATCC 53180 and *Actinomadura brunnea* ATCC 39216 are reported in Table VI.

Whole cell analysis of the microorganisms *Actinomadura brunnea* var. *antibiotica*, ATCC 53108 and ATCC 53180 found meso-diaminopimelic acid as the characteristic cell wall amino acid, trace amounts of the L, L isomer and madurose ( 3-O-methyl-D-galactose ) as the characteristic whole cell sugar.

Growth of the microorganisms *Actinomadura brunnea* var *antibiotica* ATCC 53108 and ATCC 53180 occurs from 27° to 45° C. on yeast-dextrose agar. Slight growth occurs at 50° C., the strains survive for 8 hours at 50° C. and no growth occurs at 10° C. Optimum growth is observed at about 35° C.

TABLE IV

Growth Characteristics of *Actinomadura brunnea* var. antibiotica ATCC 53108 and *Actinomadura brunnea* var. antiobiotica ATCC 53180 on Various Standard Descriptive Media

| Medium | Growth Characteristics[a,b] | |
|---|---|---|
| | ATCC 53108 | ATCC 53180 |
| Bennett's Agar | G: +, Fair | +, Fair |
| | S: Flat, granular | slightly raised |
| | AM: Present; slight, gray white | Absent |
| | DFP: Absent | Absent |
| | C: g 2 ig, slate tan | g 2 lg, mustard tan |
| Czapek Sucrose Agar | G: ++, Moderate | +, Fair |
| | S: Flat, granular | Flat |
| | AM: Absent | Absent |
| | DFP: Present; faint brown | Absent |
| | C: g 4 lg, lt. spice brown | g 5 gc, peach tan |
| Glucose Asparagine Agar | G: +, Fair | +, Fair |
| | S: Flat, granular | slightly raised |
| | AM: Absent | Absent |
| | DFP: Absent | Absent |
| | C: g 3 ie, tan | g 5 ga, salmon pink |
| Glycerol Asparagine Agar (ISP #5) | G: ++, Moderate | ++, Moderate |
| | S: Flat, granular | Raised, powdery |
| | AM: Present; slight, pink white | Present, pink white |
| | DFP: Present; faint brown | Absent |
| | C: g 4 ie, cork tan | g 6 ga, light coral |
| Nutrient Agar | G: ++, Moderate | ++, moderate |
| | S: Flat to slightly raised | Raised, folded |
| | AM: Absent | Absent |

TABLE IV-continued

Growth Characteristics of *Actinomadura brunnea* var. antibiotica ATCC 53108 and *Actinomadura brunnea* var. antiobiotica ATCC 53180 on Various Standard Descriptive Media

| Medium | | Growth Characteristics[a,b] | |
|---|---|---|---|
| | | ATCC 53108 | ATCC 53180 |
| | DFP: | Absent | Pale green brown |
| | C: | g 2 lg, mustard tan | g 2 lg, mustard tan |
| Peptone Glucose Agar | G: | +++, Good | +++, Good |
| | S: | Raised, folded | Raised, folded |
| | AM: | Absent | Absent |
| | DFP: | Absent | Absent |
| | C: | g 2 ie, lt. mustard tan | g 2 ie, mustard tan |
| Potato Dextrose Agar | G: | +++, Good | +++, Good |
| | S: | Slightly raised, folded | Raised, folded |
| | AM: | Absent | Absent |
| | DFP: | Absent | yellow-brown |
| | C: | g 2 ie, mustard tan | g 4 ic, suntan |
| Emerson's Agar | G: | +++, Good | +++, Good |
| | S: | raised, folded | Raised, folded |
| | AM: | Absent | Absent |
| | DFP: | Present; faint brown | light brown |
| | C: | g 3 nl, dark brown | g 4 le, maple |
| NZA Glucose Agar | G: | +++, Good | +++, Good |
| | S: | Raised, hard, folded | Raised, folded |
| | AM: | Absent | Absent |
| | DFP: | Present; faint brown | brown |
| | C: | g 2 lg, mustard tan | g 3 ie, camel |
| Yeast Extract Glucose Agar | G: | +++, Good | +++, Good |
| | S: | Raised, hard, folded | Raised, folded |
| | AM: | Absent | Absent |
| | DFP: | Present; brown | brown |
| | C: | g 2 pn, dark brown | g 3 ni, clove brown |
| Tomato Paste-Oatmeal Agar | G: | +++, Good | ++, Moderate |
| | S: | Raised to flat, ribbon-like | Raised, folded |
| | AM: | Absent | Present; white |
| | DFP: | Present; gray-brown | Absent |
| | C: | g 3 nl, dark brown | g 4 ig, fawn |
| Yeast Extract Malt Extract Agar (ISP #2) | G: | +++, Good | +++, Good |
| | S: | Raised, granular | Raised, folded |
| | AM: | Present; moderate gray-white | Present; pink-white |
| | DFP: | Present; faint brown | brown |
| | C: | g 4 li, beaver | 9 4 nl, chocolate |
| Oatmeal Agar (ISP #3) | G: | +, Fair | ++, Moderate |
| | S: | Flat, granular | Flat, raised |
| | AM: | Absent | Present; pink |
| | DFP: | Present; faint brown | Absent |
| | C: | g 5 ih, lead gray | g 5 gc, peach tan |
| Inorganic Salts-Starch Agar (ISP #4) | G: | ++, Moderate | ++, Moderate |
| | S: | Flat, granular | Flat, granular |
| | AM: | Absent | Absent |
| | DFP: | Absent | Absent |
| | C: | g 3 ig, beige brown | g 3 ie, camel |
| Starch Agar (Waksman #21) | G: | +, Fair | +, Fair |
| | S: | Flat, granular | Raised, smooth |
| | AM: | Absent | Absent |
| | DFP: | Present; faint brown | Absent |
| | C: | g 4 ie, cork tan | g 5 ea, peach pink |
| Calcium Maleate Agar (Waksman #7) | G: | +, Fair | +, Fair |
| | S: | Flat, granular | Raised, folded |
| | AM: | Absent | Absent |
| | DFP: | Absent | Absent |
| | C: | g 3 ng, yellow maple | g 4 ga, apricot |
| Peptone Iron Agar | G: | +++, Good | +++, Good |
| | S: | Raised, hard, granular | Raised, folded |
| | AM: | Absent | Absent |
| | DFP: | Present; faint brown | Absent |
| | C: | g 3 li, beaver | g 3 ec, bisque |
| Tyrosine Agar (ISP #7) | G: | +, Fair | +, Fair |
| | S: | Flat, granular | Flat, granular |
| | AM: | Absent | Present; gray-white |
| | DFP: | Absent | Absent |
| | C: | g 3 ig, beige brown | g 4 gc, nude tan |
| Starch Yeast Agar | G: | +++, Good | +++, Good |
| | S: | Raised, folded, cracking | Raised, folded |
| | AM: | Present; slight, gray | Present; gray-white |
| | DFP: | Present; faint brown | Present; faint brown |
| | C: | g 3 ml, beaver gray | g 3 lg, adobe brown |

[a] G = Growth; S = Surface Characteristics; AM = Aerial Mycelia DFP = Diffusible Pigments; and C = Color
[b] after 14–21 days at 30° C.

TABLE V

CARBOHYDRATE UTILIZATION[1] OF *A. brunnea* var. antiobiotica ATCC 53180 and *A. brunnea* var antiobiotica ATCC 53180 and *A. brunnea* ATCC 39216

| | Result | |
|---|---|---|
| Utilization of: | *A. brunnea* var. antibiotica ATCC 53108 and ATCC 53108 | *A. brunnea*, ATCC 39216 |
| Adonitol | ++, Moderate | +++, Good |
| D-Arabinose | ++, Moderate | ++, Moderate |
| L-Arabinose | ++, Moderate | +++, Good |
| Cellibiose | +++, Good | +++, Good |
| Dextrin | ++, Moderate | +++, Good |
| Dulcitol | −, Poor | −, Poor |
| Erythritol | −, Poor | −, Poor |
| Fructose | −, Poor | −, Poor |
| L-Fucose | +++, Good | ++, Good |
| Galactose | −, Poor | −, Poor |
| Glucose | +++, Good | +++, Good |
| α-m-d-glucoside | −, Poor | −, Poor |
| m-β-d-glucoside | −, Poor | −, Poor |
| Glycerol | +++, Good | +++, Good |
| Inositol | ++, Moderate | ++, Moderate |
| Inulin | −, Poor | −, Poor |
| Lactose | −, Poor | −, Poor |
| Maltose | +++, Good | +++, Good |
| Mannitol | −, Poor | −, Poor |
| Mannose | +++, Good | ++, Good |
| Melibiose | −, Poor | −, Poor |
| Melizitose | −, Poor | −, Poor |
| Raffinose | −, Poor | −, Poor |
| Rhamnose | ++, Moderate | ++, Moderate |
| Ribose | +++, Good | +++, Good |
| Sucrose | +++, Good | +++, Good |
| Trehalose | ++, Moderate | +++, Good |

TABLE V-continued

CARBOHYDRATE UTILIZATION[1] OF *A. brunnea* var. antibiotica ATCC 53180 and *A. brunnea* var antibiotica ATCC 53180 and *A. brunnea* ATCC 39216

| Utilization of: | Result | |
|---|---|---|
| | *A. brunnea* var. antibiotica ATCC 53108 and ATCC 53108 | *A. brunnea*, ATCC 39216 |
| D-Xylose | −, Poor | −, Poor |

[1]) Medium of Luedemann and Brodsky (Antimicrob. Ag. Chemoth. 1965)

TABLE VI

PHYSIOLOGIC CHARACTERISTICS OF *A. brunnea* var. antibiotica ATCC 53108 and *A. brunnea* var. antibiotica ATCC 53180 and *A. brunnea* ATCC 39216

| Test | Result | |
|---|---|---|
| | *A. brunnea* var antibiotica ATCC 53108 and ATCC 53180 | *A. brunnea* ATCC 39216 |
| Utilization of Organic Acids | | |
| Acetate | + | + |
| Benzoate | − | − |
| Butyrate | + | + |
| Citrate | + | + |
| Formate | + | + |
| Glucuronate | − | − |
| Glutamate | + | + |
| Lactate | − | − |
| Proprionate | + | + |
| Succinate | + | + |
| Pyruvate | + | + |
| Growth in the Presence of 50 mcg/ml | | |
| Gentamicin | + | + |
| Sisomicin | − | − |
| Neomycin | + | + |
| Kanamycin | + | + |
| Streptomycin | ± | + |
| Rosaramicin | ± | ± |
| Erythromycin | + | ± |
| Lincomycin | + | + |
| Clindamycin | + | + |
| Tetracycline | + | + |
| Growth in the Presence of 50 mcg/ml | | |
| Penicillin G | + | + |
| Cephalothin | + | + |
| Everninomicin | + | + |
| | ATCC 53108 / ATCC 53180 | |
| Rifamycin | − / + | + |
| Hydrolysis of | | |
| Adenine | − | − |
| Hyposanthine | + | + |
| Tyrosine | + | + |
| Xanthine | − | − |
| Xylan | − | − |
| Casein | + | + |
| Gelatin | + | + |
| Starch | + | + |
| Hippurate | − | − |
| Esculin | + | + |
| Breakdown of | | |
| Urea | + | + |
| Allantoin | − | − |
| Nitrate to Nitrite | − | − |
| Growth at | | |
| 10° C. | −, no growth | −, no growth |
| 27° C. | ++, moderate | ++, moderate |
| 35° C. | +++, good | +++, good |
| 40° C. | +++, good | ++, moderate |
| 45° C. | +, fair to mod. | +, fair |
| 50° C. | ±, slight | ±, slight |
| Survival | | |
| 50° C./8 hr. | + | + |

TABLE VI-continued

PHYSIOLOGIC CHARACTERISTICS OF *A. brunnea* var. antibiotica ATCC 53108 and *A. brunnea* var. antibiotica ATCC 53180 and *A. brunnea* ATCC 39216

| Test | Result | |
|---|---|---|
| | *A. brunnea* var antibiotica ATCC 53108 and ATCC 53180 | *A. brunnea* ATCC 39216 |
| Growth in the Presence of | | |
| NaCl 1% | +++, good | +++, good |
| 2% | ++, moderate | ++, moderate |
| 3% | +, fair | ++, moderate |
| 4% | ±, poor | ±, poor |
| Formation of | | |
| H₂S | − | − |
| Melanin | − | − |
| Breakdown of | | |
| Loefflers Serun | − | − |
| Dorset's Egg | − | − |

*Actinomadura brunnea* var. *antibiotica* ATCC 53108, but not ATCC 53180, differs from the parent strain, *A. brunnea* ATCC 39216, in sensitivity to rifamycin (ATCC 53108 is very sensitive to this antibiotic while the parent strain, ATCC 39216, and *A. brunnea* var. *antibiotica* ATCC 53180 are not), in vegetative mycelial pigmentation and degree of growth on some descriptive media and in the production of the antibiotic-7-chloro-8-methoxytetracycline. The mutant strains (ATCC 53108 and ATCC 53180) and the parent microorganism (ATCC 39216) produce 2'-N-methyl-7-chloro-8-methoxytetracycline.

On the basis of these morphological, physiological and culture characteristics, as well as on the production of the novel 7-chloro-8-methoxytetracycline of this invention, the microorganisms of this invention have the identifying characteristics of ATCC 53108 and 53180, and are induced mutational variants of *A. brunnea* ATCC 39216. Thus, the microorganisms of this invention, ATCC 53108 and ATCC 53180, are considered new varieties of *A. brunnea* ATCC 39216.

It is understood that in accordance with the rules of Nomenclature of Bacteria (S.P. Lapage et al. Ed. 1975, *International Code of Nomenclature of Bacteria*, 1976 revision) *A. brunnea* var. *antibiotica* is the type strain and that should another strain be found, the type strain would also be the type subspecies.

FERMENTATION OF THE MICROORGANISMS

Antibiotic ES-119 and antibiotic Tet. 7 are produced when the elaborating microorganism, *Actinomadura brunnea* var. *antibiotica* ATCC 53108 and *Actinomadura brunnea* var. *antibiotica*, ATCC 53180 respectively, are grown in an aqueous nutrient medium under submerged aerobic conditions at a temperature of about 27° C. to 45° C. preferably at from 27° C. to 35°C., and at a pH of from about 6.5 to 8.0 with agitation until substantial antibiotic activity is imparted to the medium. Temperature studies indicate that the organism grows more rapidly at 35° C. than at 30° C. Antibiotic production is greater if the temperature is lowered to 30° C. at the end of the exponential growth period at 35°. Accordingly, fermentation may also be conducted employing a two temperature pattern of 35° C. for the first 24 hours and 30° C. for the period 24 to 96 hours. However, for convenience the fermentation is generally conducted employing a single temperature pattern of 30° C. for the first 48 hours as well as for the period 24 to 96 hours.

The fermentation is generally conducted from 3 to 7 days although preferably for 4 days. To determine when peak antibiotic production has been reached, samples of the medium were assayed every 24 hours (starting at 18 hours) for antibiotic content by bioassay of the whole broth against *S. aureus*, ATCC 209P (pH 8.0) and *E. coli*, OLA 290R5 (pH 8.0). The growth of the organisms (packed cell volume), pH and dissolved oxygen levels may be determined either intermittantly or continuously.

As nutrient medium, there is employed any suitable medium containing a source of carbon, for example an assimilable carbohydrate, and a source of nitrogen, for example an assimilable nitrogenous or proteinaceous medium.

The medium employed for the inoculum stages of the fermentation contained beef and yeast extracts, cerelose and soluble starch as the major sources of nitrogen and carbon. Replacement of the beef yeast, extract by NZ-Amine A (an enzymatic hydrolysate of casein) and adjusting the amounts of cerelose and soluble starch and addition of cobalt chloride produces a medium preferred for the fermentation stage especially for large scale fermentations. Under these conditions the microorganism ATCC 53108 produced antibiotic ES-119 containing a 60:40 mixture of 7-chloro-8-methoxy-2'-N-methyltetracycline and 7-chloro-8-methoxytetracycline (the compound of this invention ) and ATCC 53180 produced antibiotic Tet. 7 containing the compound of this invention substantially free of 7-chloro-8-methoxy-2'-N-methyltetracycline, respectively, as determined by bioautography against both *S. aureus*, ATCC 209P and *E. coli*, OLA 290R5 of the antibiotic after development of a thin layer chromatography plate in, for example, 2:2:1 (v/v/v) chlorofrom: methanol: 0.2M sodium acetate buffer, pH 3.5 lower phase.

The foregoing media are exemplary of the nutrients utilized by *Actinomadura brunnea* var. *antibiotica* ATCC 53108 and *Actinomadura brunnea* var *antibiotica* ATCC 53180 to produce antibiotic ES-119 and antibiotic Tet. 7, respectively. However, it is obvious to those skilled in the fermentation art that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 6.7.

The fermentation was initiated by addition of the inoculum to the broth. Generally, the inoculum volume is 5% of total broth. The inoculum was prepared by addition of a sample of the frozen whole broth to an appropriate medium. A particularly preferred medium for the 1st and 2nd inoculum stages for antibiotic ES-119 and antibiotic Tet. 7 comprises 3 g of beef extract; 5 g of tryptone; 5 g of yeast extract, 1 g of cerelose, 24 g of potato starch 2 g of calcium carbonate and optionally 1 mL of AF-1 antifoam (Antifoam B available from Dow Corning Corp., Midland, Mich. 48641). Fermentation is completed by addition of a portion (generally about 5 volume %) of the inoculum (usually the 2nd stage inoculum) to an appropriate medium. A particularly preferred medium comprises (per liter): 5 g of yeast extract; 5 g of NZ-amine A; 20 g soluble starch, 10 g of cerelose, 1 ml of 0.001M Cobalt (II) chloride, 0.4 g of calcium carbonate and optionally 1 ml of a surfactant, e.g., AF-1 Antifoam. The pH of the inoculum medium is adjusted to 7.5 prior to sterilization. The inoculum stage of the fermentation usually requires from 24 to 120 hours with 1 to 2 days preferred and is generally conducted at about 30° C. The fermentation stage usually requires 90 to 165 hours with 90 hours being preferred and is generally conducted at 30° C. with agitation a (e.g. 350 rpm) and under an air flow rate of, for example, 3.5 L/min.

EXAMPLE 1

Preparation of Antibiotic ES-119

A. Inoculum Preparation

1) First Stage

Prepare a 25 mm tube with 10 mL of the following germination medium:

| | |
|---|---|
| Beef Extract | 3 g |
| Tryptone | 5 g |
| Yeast Extract | 5 g |
| Cerelose | 1 g |
| Soluble Starch | 24 g |
| Calcium Carbonate | 2 g |
| AF-1 Antifoam[1] | 1 mL |
| Tap Water | 1000 mL |

Adjust the pH of the germination medium to 7.5. Sterilize the medium and after cooling add 0.5 mL of a frozen whole broth sample from a previously prepared inoculum to 10 mL of the medium. Incubate at 30° C. with continual agitation at 300 rpm for 48 hours.

2) Second Stage (optional)

Transfer 25 mL of the first stage germination broth to each of two liter Erlenmeyer flasks, each containing 500 mL of the initial stage germination medium which had been previously pH adjusted and sterilized. Incubate at 30° C. with continual agitation at 300 rpm for 48 hours.

B. Fermentation

To each of four two liter Erlenmeyer flasks, add 500 mL of the following medium:

| | |
|---|---|
| Yeast Extract | 5 g |
| Casein Hydrolysate (NZ-Amine A) | 5 g |
| Cerelose | 10 g |
| Soluble Starch | 20 g |
| Calcium Carbonate | 4 g |
| Cobalt (II) Chloride | $2.4 \times 10^{-4}$ g (1 mL of 0.001M) |
| AF-1 Antifoam[1] | 1 mL |
| Tap water | 1000 mL |

[1]AF-1 Antifoam is Dow Corning Antifoam B.

Adjust the pH of the medium to 6.7 and then sterilize the medium. After sterilization, adjust the pH of the medium to 7.0 with a sterile alkaline solution. Inoculate the fermentation broth with 25 ml of the first (or optionally of the second) stage inoculum preparation of Step A. Incubate the fermentation mixture at 30° C. with 0.35 VVM of air and 300 rpm agitation for about 96 hours.

C. Isolation

Adjust the pH of the whole fermentation broth of step B to 2 with sulfuric acid and remove the insoluble mycelia by centrifugation. Extract 2 L of centrifugate at pH 2 twice with 2 L of water-saturated n-butanol. Combine the n-butanol solutions and remove the solvent by vacuum stripping at 40° C. to give a residue. Dissolve the residue in 16 mL of water and pass the aqueous solution of antibiotic ES-119 through a 0.22 micron filter.

D. Isolation (Large Scale)

Adjust the pH of the whole broth of Step B to 2 and filter the insolubles. "Adjust the pH of the filtrate to 7 and pass through 7.62 cm (id)×45.72 cm (h) chromatography column containing 450 mL of XAD-16 resin (a neutral polystyrene resin available from Rohm & Haas, Philadelphia, Pa.). Elute, successively, with 3 bed volumes (1350 mL) of each of the following: 1:20, 1:3, 1:1, 3:1 (v/v) methanol: water, then pure methanol and then 500:1 (v/v), methanol:0.02N HCl.

Monitor the antibiotic activity of eluate by disc testing each fraction (0.02 mL) against *B. subtilis* and *E. coli*. Combine the appropriate fractions and evaporate the solvent under vacuum to obtain crude antibiotic ES-119.

EXAMPLE 2

Separation of Antibiotic ES-119—Purification of 7-Chloro-8-Methoxytetracycline

A. Small Scale Purification

Place the filtrate from 1(C) on a 0.78 cm×30 cm HPLC column containing μ Bondapak C-18 (a 18 carbon chain attached to a silica support available from Waters Associates, Inc., Framingham, Mass. 01701). Use a mobile phase consisting of a linear, 15 min gradient from 100% buffer A (30:60:10 (v/v/v) methanol:water:0.2 m phosphate/phosphoric acid buffer, pH 2.5) to 100% buffer B (50:20:20:10 (v/v/v/v) methanol:acetonitrile:water:0.2M phosphate/phosphoric acid buffer, pH 2.5) at a flow rate of 3.5 mL per min. Collect fractions every 20 sec. for each of the 13 runs required to process the filtrate from Example 1(C). Monitor the antibiotic activity of each fraction by disc testing each fraction against a gram-negative organism, e.g., *E. coli* and a gram-positive organism, e.g., *B. subtilis*. Pool the fractions with activity against *E. coli*, evaporate the solvent to provide a solid residue. Repeat the HPLC procedure to provide pure 7-chloro-8-methoxytetracycline having the physico-chemical data presented in Table I.

B. Large Scale Purification

Dissolve 350 mg of the 500:1 (v/v) methanol: 0.02N HCl eluate obtained from the XAD-16 resin column in 100 mL of 0.02N HCl and filter. Place the filtrate on a 7.62 cm (id)×76.2 cm (h) glass chromatography column containing 500 g of Sephadex G-25 (a cross-linked dextram, a polysaccharide, available from Pharmacia Fine Chemicals, Inc., Piscataway, N.J.) slurred in 0.02N HCl. Elute the column with 0.02N HCl. Monitor the antibiotic activity of the eluate by disc testing against gram-positive and gram-negative organisms. Combine the fractions having activity against gram-negative organisms and lyophilize them to obtain 7-chloro-8-methoxytetracycline as a solid having the physicochemical data presented in Table I.

EXAMPLE 3

Large Scale Preparation of Antibiotic ES-119 and Antibiotic Tet. 7

The following procedures are used for preparation of antibiotic ES-119 and antibiotic Tet. 7.

A. Inoculum Preparation

1) First Stage

A. Inoculum Preparation

Add 5 volume % of a frozen whole broth of *A. brunnea* var *antibiotica* ATCC 53108 or *A. brunnea* var *antibiotica* ATCC 53180 to 70 mL of the sterilized germination medium (pH 7.5) of Example 1 (A)(1) in a 300 mL Erlenmeyer shake flask. Incubate at 30° C. for 48 hrs. with continual shaking at 300 rpm.

2) Second Stage

Add 25 mL of the first stage inoculum to 2 L Erlenmeyer shake flasks each containing 500 mL of the sterilized germination medium used in the first stage of this Example. Incubate under condition described for the first stage.

B. Fermentation

Add 5 volume percent of the second stage inoculum to 11 liters of the sterilized fermentation medium (pH 7.0) of Example 1 (B) in a 14 liter fermentor. Incubate the fermentation mixture for 90 hours at 30° C. with 350 rpm agitation and an air flow rate of 3.5 L/min (with dissolved oxygen monitoring). Sample before and after inoculation and during fermentation including harvest. Check samples for pH, growth (packed volume of cells), purity and carbohydrate utilization.

Monitor activity of the fermentation by assaying the whole broth with paper discs on agar plates seeded with *S. aureus,* ATCC 209P (pH 8.0) and *E. coli,* OLA 290R5 (pH 8.0). Samples could also be monitored by bioautography after chromatography on TLC plates. Based on the whole broth analysis, both the antibiotic ES-119 and antibiotic Tet. 7 have comparable activity which reaches a maximum in both cases at 90 hours. The antibiotic ES-119 contains about 10 mg/L of 7-chloro-8-methoxytetracycline and about 15 mg/L of 7-chloro-8-methoxy-2'-N-methyltetracycline. The antibiotic Tet. 7 contains somewhat less of the compound of this invention than found in antibiotic ES-119. No 7-chloro-8-methoxy- 2'-N-methyltetracycline was detected (e.g., less than about 1%) by TLC vs a known sample in antibiotic Tet. 7.

D. Isolation

Adjust the pH of the whole broth (60 L) from step C of this Example to 4.5 and filter. Pass the filtrate through a 121.92 cm(h)×12.7 cm(id) chromatography column containing 6 L of XAD-4 resin. Elute successively with 1:3, 1:1 (v/v) methanol: water ad 100% methanol. Monitor the antibiotic activity by disc testing the fraction against *S. aureus* and *E. coli*. Combine the fractions having biological activity and evaporate to give a solid residue. Redissolve the residue in distilled water and lyophilize to give a solid.

Treat the solid with EDTA in water and extract the water phase at pH 6.5 with methylene chloride. Evaporate the organic solvent to give a solid. Adsorb the solid on a Sephadex G-25 column, eluting with 0.02N HCl. Combine the active fractions.

Formulations

EXAMPLE 4

Parenteral Formulation

Per vial: 7-chloro-8-methoxytetracycline (hereinafter "drug") as a sterile powder. Unit dosages, may be 100 mg, 200 mg, 500 mg, 1 g and 2 g. Add sterile water for injection U.S.P. or bacteriostatic water for injection U.S.P., for reconsitution.

EXAMPLE 5

| Item No. | Capsule Formulation Ingredient | mg/capsule | mg/capsule |
|---|---|---|---|
| 1 | Drug | 100 | 200 |
| 2 | Lactose | 122 | 244 |
| 3 | Corn Starch, Dried | 25.5 | 51 |
| 4 | Magnesium Stearate | 2.5 | 5 |
| | | 250 mg | 500 mg |

Method

Mix Item Nos. 1, 2, and 3 in a suitable mixer for 10–15 minutes. Add Item No. 4 and mix for 1–3 minutes. Fill the above mixture in two-piece hard gelatin capsules of required size.

EXAMPLE 6

| Item No. | Tablet Formulation Ingredient | mg/capsule | mg/capsule |
|---|---|---|---|
| 1 | Drug | 125 | 250 |
| 2 | Lactose | 93.75 | 187.5 |
| 3 | Corn Starch (as a 10% Paste) | 5 | 10 |
| 4 | Corn Starch, Dried | 25 | 50 |
| 5 | Magnesium Stearate | 1.25 | 2.5 |
| | | 250 mg | 500 mg |

Method

Mix Item Nos. 1, 2 and a portion of Item No. 4 in a suitable mixer for 10–15 minutes. Granulate the mixture with Item No. 3. Pass the wet granulation through a coarse screen (e.g., ¼" if needed, and dry the wet granules. Mill the dried granules using a suitable milling machine. Add Item No. 5 and the remaining amount of Item No. 4. with the dried granules in a suitable blender. Mix for 5–10 minutes. Compress the mixture into the tablets of required shape and size on a rotary tablet machine. The tablets may be coated using standard coating procedures.

EXAMPLE 7

| Item No. | Topical Formulation Ingredient | mg/g |
|---|---|---|
| 1 | Drug | 25 |
| 2 | Ethyl Alcohol | 400 |
| 3 | Hydroxypropyl Cellulose | 15 |
| 4 | Polyethylene Glycol 400 | 560 |

Mix Item Nos. 1,2 and 4 in a suitable mixer. Stir vigorously and charge Item No. 3. Maintain stirring until uniformity is achieved.

EXAMPLE 8

| Item No. | Oral Powder for Reconstitution (I) Part A (Powder Formulation) Ingredient | mg/g |
|---|---|---|
| 1 | Drug | 46.3 |
| 2 | Flavor(s) | q.s. |
| 3 | Colorant | q.s. |
| 4 | Preservative | q.s. |
| 5 | Buffer Agents | q.s. |
| 6 | Sugar | q.s. |
| | To make | 1.0 g |

Mix Item Nos. 1, 2, 3, 4 and 5 thoroughly. Charge Item No. 6 and mix until uniformity is achieved.

Part B (Reconstitution)

Charge 54 g of above formulated powder into a proper container and add enough water to make up 100 ml. Shake well after the addition of water. Each 5 ml (1 teaspoonful) will then contain drug equivalent to 125 mg.

EXAMPLE 9

| Item No. | Oral Powder for Reconstitution (II) Part A (Powder Formulation) Ingredient | mg/g |
|---|---|---|
| 1 | Drug | 416.7 |
| 2 | Flavor(s) | q.s. |
| 3 | Colorant | q.s. |
| 4 | Preservative | q.s. |
| 5 | Buffering Agents | 28.3 |
| 6 | Saccharin | q.s. |
| 7 | PVP | |
| | To make | 1.0 g |

Mix Item Nos. 1, 2, 3, 4, 5, 6, and 7 well until uniform.

Part B (Reconstitution)

Charge 6.0 g of above powder into a suitable container and add enough water to make up 100 ml. Shake well until uniform. Each 5 ml will then contain drug equivalent to 125 mg.

EXAMPLE 10

| Item No. | Oral Liquid Ingredient | mg/ml |
|---|---|---|
| 1 | Drug | 25.0 |
| 2 | Sweetner | q.s. |
| 3 | Flavor | q.s. |
| 4 | Colorant | q.s. |
| 5 | Vegetable Oil | q.s. |
| | To make | 1.0 ml |

Charge 90% of Item No. 5 needed into a suitable container. Charge Item Nos. 1, 2, 3 and 4 and mix well. Bring to the final volume by the reserved Item No. 5.

EXAMPLE 11

| Item No. | Suppository Ingredient | Suppository |
|---|---|---|
| 1 | Drug | 125.0 |
| 2 | Witepsol H-15 | 1868 |

Melt Item No. 2 and blend Item No. 1 until uniform. Pour into mold and congeal in refrigerator. Remove suppository from mold.

We claim:

1. A biologically pure culture of the microorganism *Actinomadura brunnea* var. having all of the identifying characteristics of ATCC 53108.

2. A biologically pure culture of the microorganism *Actinomadura brunnea* var. *antibiotica* having all of the identifying characteristics of ATCC 53180.

* * * * *